(12) United States Patent
Egawa

(10) Patent No.: US 8,791,221 B2
(45) Date of Patent: Jul. 29, 2014

(54) ADDITION-CURABLE METALLOSILOXANE COMPOUND

(75) Inventor: Tomoya Egawa, Himeji (JP)

(73) Assignee: Daicel Corporation, Osaka (JP)

( * ) Notice: Subject to any disclaimer, the term of this patent is extended or adjusted under 35 U.S.C. 154(b) by 0 days.

(21) Appl. No.: 13/992,665

(22) PCT Filed: Nov. 29, 2011

(86) PCT No.: PCT/JP2011/077496
§ 371 (c)(1),
(2), (4) Date: Jun. 7, 2013

(87) PCT Pub. No.: WO2012/077529
PCT Pub. Date: Jun. 14, 2012

(65) Prior Publication Data
US 2013/0267653 A1    Oct. 10, 2013

(30) Foreign Application Priority Data

Dec. 9, 2010 (JP) .................. 2010-274245

(51) Int. Cl.
*C08G 79/08*    (2006.01)
(52) U.S. Cl.
USPC .............. 528/9; 525/477; 525/478; 528/15; 528/31; 528/32

(58) Field of Classification Search
None
See application file for complete search history.

(56) References Cited

U.S. PATENT DOCUMENTS

| | | | |
|---|---|---|---|
| 4,152,509 A | 5/1979 | Yajima et al. | |
| 4,228,270 A | 10/1980 | Kobayashi | |
| 4,841,006 A * | 6/1989 | Kobayashi et al. | 528/15 |
| 6,180,809 B1 * | 1/2001 | Pillot et al. | 556/402 |
| 6,617,401 B2 | 9/2003 | Rubinsztajn | |
| 6,716,952 B1 * | 4/2004 | Matsumoto et al. | 528/10 |
| 6,809,162 B2 | 10/2004 | Rubinsztajn | |
| 2003/0071368 A1 | 4/2003 | Rubinsztajn | |
| 2003/0208008 A1 | 11/2003 | Rubinsztajn | |
| 2005/0106400 A1 | 5/2005 | Kuramoto et al. | |
| 2009/0014750 A1 * | 1/2009 | Katayama et al. | 257/100 |
| 2010/0041851 A1 | 2/2010 | Katsoulis et al. | |
| 2010/0316876 A1 | 12/2010 | Zhu | |
| 2011/0021736 A1 | 1/2011 | Zhu | |

FOREIGN PATENT DOCUMENTS

| | | |
|---|---|---|
| DE | 4339478 A1 | 5/1995 |
| JP | 53-22051 A | 2/1977 |
| JP | 53-42300 A | 4/1978 |
| JP | 53-50299 A | 5/1978 |
| JP | 54-88247 A | 7/1979 |
| JP | 64-38473 A | 2/1989 |
| JP | 7-207161 A | 8/1995 |
| JP | 10-152561 A | 6/1998 |
| JP | 2002-265609 A | 9/2002 |
| JP | 2003-176333 A | 6/2003 |
| JP | 2005-298796 A | 10/2005 |
| JP | 2009-19104 A | 1/2009 |
| JP | 2010-518234 A | 5/2010 |
| WO | WO 95/14054 A1 | 5/1995 |
| WO | WO 2009/111191 A1 | 9/2009 |
| WO | WO 2009/111193 A1 | 9/2009 |

OTHER PUBLICATIONS

International Search Report for PCT/JP2011/077496 mailed on Feb. 14, 2012.
Extended European Search Report, dated Apr. 9, 2014, for European Application No. 11846305.8.

* cited by examiner

*Primary Examiner* — Marc Zimmer
(74) *Attorney, Agent, or Firm* — Birch, Stewart, Kolasch & Birch, LLP

(57) ABSTRACT

Provided is a metallosiloxane compound (A) prepared by reacting a bifunctional silane compound (S1), a monofunctional silane compound (S2), a boron compound (M), and optionally $H_2O$ in a molar ratio of [the silane compound (S1)]:[the silane compound (S2)]:[the boron compound (M)]:[$H_2O$] of n:m:k:a, where n, m, k, and a satisfy all conditions (i), (ii), and (iii), in which the metallosiloxane compound has at least one Si—H bond or $C_{2-10}$ alkenyl group per molecule, and the conditions (i), (ii), and (iii) are expressed as follows:
(i) n>0, m>0, k>0, a≥0;
(ii) m/n≥0.5; and
(iii) (n+m)/k≥1.8.

6 Claims, No Drawings

ADDITION-CURABLE METALLOSILOXANE COMPOUND

TECHNICAL FIELD

The present invention relates to an addition-curable metallosiloxane compound; a curable resin composition including the metallosiloxane compound; and a cured product derived from the curable resin composition.

BACKGROUND ART

Semiconductors, optoelectronics, and other solid state devices have become to be used at higher and higher currents and thereby tend to generate larger quantities of heat. Packaging materials for the encapsulation of these devices require heat resistance and durability at high levels. Among them, packaging materials for optoelectronic devices require satisfactory transparency in addition to the above properties.

To meet the requirements, resin compositions containing an inorganic compound have been being employed as resin materials that excel in properties such as heat resistance, thermal stability (resistance to thermal coloration), and transparency. Patent Literature (PTL) 1 describes cycloaliphatic epoxy resins for the encapsulation of light-emitting diodes and other solid state devices. The epoxy resins contain a boric acid ester and an alkoxysilane. The literature mentions that the resins less deteriorate upon ultraviolet irradiation over a long time. The resins, however, probably have poor resistance to thermal yellowing upon long-term exposure to elevated temperatures of 150° C. or higher, because the resins employ an epoxy resin as a principal component.

Independently, PTL 2 reports polyborosiloxane, an inorganic polymer to form an insulating layer having heat resistance, moisture resistance, and flexibility at high levels, which is obtained by reacting first a bifunctional silane compound with a boron compound to give a product, and further reacting the product with a trifunctional silane compound and a boron compound. The polyborosiloxane, however, has not been examined as an electronic-device packaging material because the polyborosiloxane is solid at room temperature and requires a solvent to form a coating film.

CITATION LIST

Patent Literature

PTL 1: Japanese Unexamined Patent Application Publication (JP-A) No. 2003-176333
PTL 2: JP-A No. H10-152561

SUMMARY OF INVENTION

Technical Problem

An object of the present invention is to provide an addition-curable metallosiloxane compound which provides satisfactory resistance to thermal yellowing and causes substantially no outgassing when contained in a curable resin composition and cured.

Another object of the present invention is to provide a curable resin composition which includes the metallosiloxane compound, causes substantially no outgassing, and, when cured, gives an inorganic cured resin resistant to thermal yellowing.

Yet another object of the present invention is to provide a cured product which is obtained by curing the curable resin composition and is resistant to thermal yellowing.

Solution to Problem

After intensive investigations to achieve the objects, the present inventor has found a novel metallosiloxane compound obtained by reacting a bifunctional silane compound, a monofunctional silane compound, a boron compound, and optionally $H_2O$ in a specific molar ratio. The present inventor has found that the metallosiloxane compound gives a curable resin composition which suffers from less or no outgassing upon curing; and that the curable resin composition gives, when cured, a cured product having satisfactory resistance to thermal yellowing. The present invention has been made based on these findings.

Specifically, the present invention provides a metallosiloxane compound as a metallosiloxane compound (A) prepared by reacting a silane compound (S1) represented by Formula (1), a silane compound (S2) represented by Formula (2), and a boron compound (M), or reacting the silane compound (S1), the silane compound (S2), the boron compound (M), and $H_2O$ in a molar ratio of [the silane compound (S1)]:[the silane compound (S2)]:[the boron compound (M)]:[$H_2O$] of n:m:k:a, where n, m, k, and a satisfy all conditions (i), (ii), and (iii), wherein the metallosiloxane compound has at least one Si—H bond or $C_{2-10}$ alkenyl group per molecule, Formula (1) expressed as follows:

[Chem. 1]

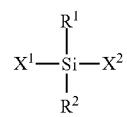

(1)

wherein $R^1$ and $R^2$ are the same as or different from each other and each represent a hydrogen atom, a $C_{1-10}$ alkyl group, a $C_{2-10}$ alkenyl group, a $C_{6-14}$ aryl group, or a $C_{7-15}$ aralkyl group; and $X^1$ and $X^2$ are the same as or different from each other and each represent a $C_{1-10}$ alkoxy group, a halogen atom, or a hydroxyl group, Formula (2) expressed as follows:

[Chem. 2]

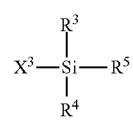

(2)

wherein $R^3$, $R^4$, and $R^5$ are the same as or different from one another and each represent a hydrogen atom, a $C_{1-10}$ alkyl group, a $C_{2-10}$ alkenyl group, a $C_{6-14}$ aryl group, or a $C_{7-15}$ aralkyl group; and $X^3$ represents a $C_{1-10}$ alkoxy group, a halogen atom, or a hydroxyl group, and the conditions (i), (ii), (iii) expressed as follows:
(i) n>0, m>0, k>0, a≥0;
(ii) m/n0.5; and
(iii) (n+m)/k≥1.8

In a preferred embodiment, the metallosiloxane compound according to the present invention is solid at a temperature in the range from 0° C. to 90° C.

The present invention further provides a curable resin composition including a compound having at least one Si—H bond; and a compound having at least one $C_{2-10}$ alkenyl group, in which the curable resin composition contains at least the metallosiloxane compound (A) and a hydrosilylation catalyst (C).

In other embodiments, the curable resin composition according to the present invention may further contain an inorganic filler (D) and/or a silane coupling agent (E).

In addition and advantageously, the present invention provides a cured product obtained by curing the curable resin composition.

Advantageous Effects of Invention

The metallosiloxane compound according to the present invention, when contained in a curable resin composition and cured, gives a curable resin composition that causes substantially no outgassing. Furthermore, the curable resin composition gives, when cured, a cured product having satisfactory resistance to thermal yellowing. They are therefore useful typically as encapsulants, sealants, and heat-resisting hard coatings for LEDs and other electronic devices.

DESCRIPTION OF EMBODIMENTS

[Metallosiloxane Compound (A)]

A metallosiloxane compound according to an embodiment of the present invention is a metallosiloxane compound (A) which is prepared by reacting a silane compound (S1) represented by Formula (1), a silane compound (S2) represented by Formula (2), and a boron compound (M), or reacting the silane compound (S1), the silane compound (S2), the boron compound (M), and $H_2O$ in a molar ratio of [the silane compound (S1)]:[the silane compound (S2)]:[the boron compound (M)]:[$H_2O$] of n:m:k:a, where n, m, k, and a satisfy all conditions (i), (ii), and (iii), in which the metallosiloxane compound has at least one Si—H bond or $C_{2-10}$ alkenyl group per molecule, Formula (1) expressed as follows:

[Chem. 1]

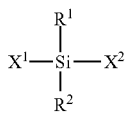
(1)

wherein $R^1$ and $R^2$ are the same as or different from each other and each represent a hydrogen atom, a $C_{1-10}$ alkyl group, a $C_{2-10}$ alkenyl group, a $C_{6-14}$ aryl group, or a $C_{7-15}$ aralkyl group; and $X^1$ and $X^2$ are the same as or different from each other and each represent a $C_{1-10}$ alkoxy group, a halogen atom, or a hydroxyl group, Formula (2) expressed as follows:

[Chem. 2]

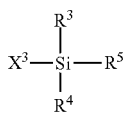
(2)

wherein $R^3$, $R^4$, and $R^5$ are the same as or different from one another and each represent a hydrogen atom, a $C_{1-10}$ alkyl group, a $C_{2-10}$ alkenyl group, a $C_{6-14}$ aryl group, or a $C_{7-15}$ aralkyl group; and $X^3$ represents a $C_{1-10}$ alkoxy group, a halogen atom, or a hydroxyl group, and the conditions (i), (ii), (iii) expressed as follows:
(i) n>0, m>0, k>0, a≥0;
(ii) m/n≥0.5; and
(iii) (n+m)/k≥1.8

The $C_{2-10}$ alkenyl group to be contained in a number of at least one in the metallosiloxane compound according to the present invention is exemplified by vinyl, allyl, 2-butenyl, 2-pentanyl, and 2-hexynyl groups. Among them, vinyl and allyl groups are preferred as the $C_{2-10}$ alkenyl group. When two or more different silane compounds (S1), two or more different silane compounds (S2), and/or two or more different boron compounds (M) are used as described below, each of the molar ratios n, m, and/or k refers to the molar ratio of the total of the two or more different compounds.

The present invention employs what is hereafter described as a monofunctional silane compound (S2) and a bifunctional silane compound (S1) in a molar ratio of the former to the latter of 0.5 or more, in which the molar ratio of the total moles of the bifunctional and monofunctional silane compounds to the moles of the boron compound (M) is 1.8 or more. The silane compound (S2) has one functional group ($X^3$) selected from the group consisting of a hydrolyzable group and a hydroxyl group per molecule. The silane compound (S1) has two functional groups ($X^1$ and $X^2$) selected from the group consisting of hydrolyzable groups and hydroxyl groups per molecule. A reaction of components in such molar ratios can give a metallosiloxane compound which is liquid preferably at a temperature in the range from 0° C. to 90° C., and upon curing, which is resistant to outgassing and gives a cured product resistant to thermal yellowing.

The silane compounds (S1) and (S2) represented by Formulae (1) and (2) are herein also referred to as "bifunctional silane compound (S1)" and "monofunctional silane compound (S2)", respectively. A silane compound including at least one Si—H bond is also referred to as an "H-type" silane compound; a silane compound including at least one $C_{2-10}$ alkenyl group (e.g., vinyl or allyl group) is referred to as a "vinyl-type" silane compound; and a silane compound including neither Si—H bond nor $C_{2-10}$ alkenyl group is referred to as an "other" silane compound.

The monofunctional silane compound (S2) and the bifunctional silane compound (S1) may be used herein in a molar ratio m/n of the former to the latter of preferably 0.5 or more and 5 or less, more preferably 0.6 or more and 3 or less, and particularly preferably 0.6 or more and 1.5 or less. When the molar ratio m/n is 0.6 or more and 1.5 or less, the molar ratio (n:m) of the bifunctional silane compound (S1) to the monofunctional silane compound (S2) is from 0.7:1 to 1.7:1. The molar ratio of the total moles of the bifunctional and monofunctional silane compounds to the moles of the boron compound (M) may be preferably 1.8 or more and 10 or less [(n+m)/k is 1.8 to 10], more preferably 1.8 or more and 5 or less [(n+m)/k is 1.8 to 5], and particularly preferably 1.8 or more and 3.5 or less [(n+m)/k is 1.8 to 3.5].

The reaction among the bifunctional silane compound (S1), the monofunctional silane compound (S2), the boron compound (M), and optionally $H_2O$ may be performed in one step (single-step reaction) or in two steps (two-step reaction). The single-step reaction is performed using a reaction mixture containing all the compounds. The two-step reaction includes a first step and a second step. The first step is the step of pre-reacting the bifunctional silane compound (S1), the boron compound (M), and optionally H₂O to give a reaction mixture. The second step is the step of adding to and reacting with the reaction mixture, the monofunctional silane compound (S2), optionally the bifunctional silane compound (S1) and the boron compound (M), and optionally H₂O.

The two-step reaction is probably carried out so that boron atom and silicon atom are combined with each other by the medium of oxygen atom to form a principal chain in the first step; and silyl group derived from the monofunctional silane compound (S2) is introduced into a side chain to give a metallosiloxane compound in the second step. Among these reactions, the two-step reaction is preferred because the introduction of boron and silicon atoms in a principal chain of a metallosiloxane compound helps the resulting metallosiloxane compound to be liquid and to often give, when cured, a cured product highly resistant to thermal yellowing.

The reaction may be performed at a temperature of typically 50° C. to 150° C., preferably 60° C. to 130° C., and more preferably 60° C. to 100° C. The reaction may also be performed for a time of typically 10 minutes to 10 hours and preferably 1 to 5 hours, while the reaction time may vary depending on the reaction temperature and the types of the silane compounds and boron compound to be used. The two-step reaction may be performed at a reaction temperature as above for a reaction time in the first step of typically 1 minute to 5 hours and preferably 10 minutes to one hour and for a reaction time in the second step of typically 10 minutes to 10 hours and preferably 1 to 5 hours.

The metallosiloxane compound (A) produced by the production process may be liquid at a temperature in the range of preferably from 0° C. to 90° C., more preferably from 0° C. to 70° C., and particularly preferably from 0° C. to 30° C.

The metallosiloxane compound according to the present invention is an oligomer or polymer obtained by hydrolytic co-condensation of a boron compound (M) (e.g., an alkoxide, halide, or hydroxide of boron) with an alkoxide, halide, or hydroxide of silicon. The metallosiloxane compound (A) according to the present invention may have a weight-average molecular weight Mw of preferably 500 to 100000 and more preferably 500 to 30000. Control of the Mw within this range may easily give a liquid metallosiloxane.

[Bifunctional Silane Compound (S1)]

The bifunctional silane compound (S1) for use in the reaction to form the metallosiloxane compound (A) according to the present invention is represented by following Formula (1)

[Chem. 5]

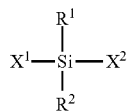

(1)

wherein $R^1$ and $R^2$ are the same as or different from each other and each represent a hydrogen atom, a $C_{1-10}$ alkyl group, a $C_{2-10}$ alkenyl group, a $C_{6-14}$ aryl group, or a $C_{7-15}$ aralkyl group; and $X^1$ and $X^2$ are the same as or different from each other and each represent a $C_{1-10}$ alkoxy group, a halogen atom, or a hydroxyl group. Such bifunctional silane compounds (S1) usable herein include known dialkoxysilane compounds, dihalogenated silane compounds, and dihydroxysilane compounds customarily used in productions to form polysiloxanes and polyborosiloxanes.

As for $R^1$ and $R^2$ in Formula (1), the $C_{1-10}$ alkyl group is exemplified by methyl, ethyl, propyl, isopropyl, butyl, isobutyl, s-butyl, t-butyl, hexyl, octyl, and decyl groups; the $C_{2-10}$ alkenyl group is exemplified by vinyl, allyl, 2-butenyl, 2-pentanyl, and 2-hexynyl groups; the $C_{6-14}$ aryl group is exemplified by phenyl and naphthyl groups; and the $C_{7-15}$ aralkyl group is exemplified by benzyl group.

As for $X^1$ and $X^2$ in Formula (1), the $C_{1-10}$ alkoxy group is exemplified by methoxy, ethoxy, propoxy, and butoxy groups; and the halogen atom is exemplified by fluorine, chlorine, and bromine atoms.

Of dialkoxysilane compounds, H-type dialkoxysilane compounds are exemplified by di($C_{1-10}$ alkoxy)silane compounds including two hydrogen atoms, such as dimethoxysilane, diethoxysilane, dipropoxysilane, and dibutoxysilane; and di($C_{1-10}$ alkoxy)silane compounds including one hydrogen atom, such as methyldimethoxysilane, methyldiethoxysilane, methyldipropoxysilane, methyldibutoxysilane, ethyldimethoxysilane, ethyldiethoxysilane, ethyldipropoxysilane, ethyldibutoxysilane, propyldimethoxysilane, propyldiethoxysilane, propyldipropoxysilane, propyldibutoxysilane, butyldimethoxysilane, butyldiethoxysilane, butyldipropoxysilane, butyldibutoxysilane, phenyldimethoxysilane, phenyldiethoxysilane, phenyldipropoxysilane, phenyldibutoxysilane, naphthyldimethoxysilane, naphthyldiethoxysilane, naphthyldipropoxysilane, naphthyldibutoxysilane, benzyldimethoxysilane, benzyldiethoxysilane, benzyldipropoxysilane, and benzyldibutoxysilane.

Vinyl-type dialkoxysilane compounds are exemplified by di($C_{2-10}$ alkenyl)di($C_{1-10}$ alkoxy)silane compounds such as divinyldimethoxysilane, diallyldimethoxysilane, di(2-butenyl)propyldimethoxysilane, di(2-pentanyl)dimethoxysilane, divinyldiethoxysilane, diallyldiethoxysilane, di(2-butenyl)propyldiethoxysilane, di(2-pentanyl)diethoxysilane, divinyldipropoxysilane, diallyldipropoxysilane, di(2-butenyl)propyldipropoxysilane, di(2-pentanyl)dipropoxysilane, divinyldibutoxysilane, diallyldibutoxysilane, di(2-butenyl)propyldibutoxysilane, and di(2-pentanyl)dibutoxysilane; ($C_{1-10}$ alkyl)($C_{2-10}$ alkenyl)di($C_{1-10}$ alkoxy)silane compounds such as methyl(vinyl)dimethoxysilane, ethyl(vinyl)dimethoxysilane, propyl(vinyl)dimethoxysilane, butyl(vinyl)dimethoxysilane, methyl(vinyl)diethoxysilane, ethyl(vinyl)diethoxysilane, propyl(vinyl)diethoxysilane, butyl(vinyl)diethoxysilane, methyl(allyl)dimethoxysilane, ethyl(allyl)dimethoxysilane, propyl(allyl)dimethoxysilane, butyl(allyl)dimethoxysilane, methyl(allyl)diethoxysilane, ethyl(allyl)diethoxysilane, propyl(allyl)diethoxysilane, and butyl(allyl)diethoxysilane; ($C_{6-14}$ aryl)($C_{2-10}$ alkenyl)di($C_{1-10}$ alkoxy)silane compounds such as phenyl(vinyl)dimethoxysilane, naphthyl(vinyl)dimethoxysilane, phenyl(vinyl)diethoxysilane, naphthyl(vinyl)diethoxysilane, phenyl(vinyl)dipropoxysilane, naphthyl(vinyl)dipropoxysilane, phenyl(vinyl)dibutoxysilane, naphthyl(vinyl)dibutoxysilane, phenyl(allyl)dimethoxysilane, naphthyl(allyl)dimethoxysilane, phenyl(allyl)diethoxysilane, naphthyl(allyl)diethoxysilane, phenyl(allyl)dipropoxysilane, naphthyl(allyl)dipropoxysilane, phenyl(allyl)dibutoxysilane, and naphthyl(allyl)dibutoxysilane; and ($C_{7-15}$ aralkyl)($C_{2-10}$ alkenyl)di($C_{1-10}$ alkoxy)silane compounds such as benzyl(vinyl)dimethoxysilane, benzyl(vinyl)diethoxysilane, benzyl(vinyl)dipropoxysilane, benzyl(vinyl)dibutoxysilane, benzyl(allyl)dimethoxysilane, benzyl(allyl)diethoxysilane, benzyl(allyl)dipropoxysilane, and benzyl(allyl)dibutoxysilane.

Other dialkoxysilane compounds are exemplified by di($C_{1-10}$ alkyl)di($C_{1-10}$ alkoxy)silane compounds such as dimethyldimethoxysilane, diethyldimethoxysilane, dipropyldimethoxysilane, dibutyldimethoxysilane, dimethyldiethoxysilane, diethyldiethoxysilane, dipropyldiethoxysilane, dibutyldiethoxysilane, dimethyldipropoxysilane, diethyldipropoxysilane, dipropyldipropoxysilane, dibutyldipropoxysilane, dimethyldibutoxysilane, diethyldibutoxysilane, dipropyldibutoxysilane, and dibutyldibutoxysilane; di($C_{6-14}$ aryl)di($C_{1-10}$ alkoxy)silane compounds such as diphenyldimethoxysilane, dinaphthyldimethoxysilane, diphenyldiethoxysilane, dinaphthyldiethoxysilane, diphenyldipropoxysilane, dinaphthyldipropoxysilane, diphenyldibutoxysilane, and dinaphthyldibutoxysilane; di($C_{7-15}$ aralkyl)di($C_{1-10}$ alkoxy)silane compounds such as dibenzyldimethoxysilane, dibenzyldiethoxysilane, dibenzyldipropoxysilane, and dibenzyldibutoxysilane; ($C_{1-10}$ alkyl)($C_{6-14}$ aryl)di($C_{1-10}$ alkoxy)silane compounds such as methyl(phenyl)dimethoxysilane, ethyl(phenyl)dimethoxysilane, propyl(phenyl)dimethoxysilane, butyl(phenyl)dimethoxysilane, methyl(phenyl)diethoxysilane, ethyl(phenyl)diethoxysilane, propyl(phenyl)diethoxysilane, butyl(phenyl)diethoxysilane, methyl(naphthyl)dimethoxysilane, ethyl(naphthyl)dimethoxysilane, propyl(naphthyl)dimethoxysilane, butyl(naphthyl)dimethoxysilane, methyl(naphthyl)diethoxysilane, ethyl(naphthyl)diethoxysilane, propyl(naphthyl)diethoxysilane, and butyl(naphthyl)diethoxysilane; and ($C_{1-10}$ alkyl)($C_{7-15}$ aralkyl)di($C_{1-10}$ alkoxy)silane compounds such as methyl(benzyl)dimethoxysilane, ethyl(benzyl)dimethoxysilane, propyl(benzyl)dimethoxysilane, butyl(benzyl)dimethoxysilane, methyl(benzyl)diethoxysilane, ethyl(benzyl)diethoxysilane, propyl(benzyl)diethoxysilane, and butyl(benzyl)diethoxysilane.

H-type dihalogenated silane compounds are exemplified by dihalogenated silane compounds including two hydrogen atoms, such as difluorosilane, dichlorosilane, and dibromosilane; and dihalogenated silane compounds including one hydrogen atom, such as difluoro(methyl)silane, dichloro(methyl)silane, dibromo(methyl)silane, difluoro(ethyl)silane, dichloro(ethyl)silane, dibromo(ethyl)silane, difluoro(propyl)silane, dichloro(propyl)silane, dibromo(propyl)silane, difluoro(butyl)silane, dichloro(butyl)silane, dibromo(butyl)silane, difluoro(phenyl)silane, dichloro(phenyl)silane, dibromo(phenyl)silane, difluoro(naphthyl)silane, dichloro(naphthyl)silane, dibromo(naphthyl)silane, fluoro(benzyl)silane, dichloro(benzyl)silane, and dibromo(benzyl)silane.

Vinyl-type dihalogenated silane compounds are exemplified by dihalogenated di($C_{2-10}$ alkenyl)silane compounds such as difluorodivinylsilane, dichlorodivinylsilane, dibromodivinylsilane, difluorodiallylsilane, dichlorodiallylsilane, dibromodiallylsilane, difluorodi(2-butenyl)silane, dichlorodi(2-butenyl)silane, dibromodi(2-butenyl)silane, difluorodi(2-pentanyl)silane, dichlorodi(2-pentanyl)silane, and dibromodi(2-pentanyl)silane; dihalogenated ($C_{1-10}$ alkyl)($C_{2-10}$ alkenyl)silane compounds such as difluoro(methyl)vinylsilane, difluoro(ethyl)vinylsilane, difluoro(propyl)vinylsilane, difluoro(butyl)vinylsilane, dichloro(methyl)vinylsilane, dichloro(ethyl)vinylsilane, dichloro(propyl)vinylsilane, dichloro(butyl)vinylsilane, dibromo(methyl)vinylsilane, dibromo(ethyl)vinylsilane, dibromo(propyl)vinylsilane, dibromo(butyl)vinylsilane, difluoro(methyl)allylsilane, difluoro(ethyl)allylsilane, difluoro(propyl)allylsilane, difluoro(butyl)allylsilane, dichloro(methyl)allylsilane, dichloro(ethyl)allylsilane, dichloro(propyl)allylsilane, dichloro(butyl)allylsilane, dibromo(methyl)allylsilane, dibromo(ethyl)allylsilane, dibromo(propyl)allylsilane, and dibromo(butyl)allylsilane; dihalogenated ($C_{6-14}$ aryl)($C_{2-10}$ alkenyl)silane compounds such as difluoro(phenyl)vinylsilane, difluoro(naphthyl)vinylsilane, dichloro(phenyl)vinylsilane, dichloro(naphthyl)vinylsilane, dibromo(phenyl)vinylsilane, dibromo(naphthyl)vinylsilane, difluoro(phenyl)allylsilane, difluoro(naphthyl)allylsilane, dichloro(phenyl)allylsilane, dichloro(naphthyl)allylsilane, dibromo(phenyl)allylsilane, and dibromo(naphthyl)allylsilane; and dihalogenated ($C_{7-15}$ aralkyl)($C_{2-10}$ alkenyl)silane compounds such as difluoro(benzyl)vinylsilane, dichloro(benzyl)vinylsilane, dibromo(benzyl)vinylsilane, difluoro(benzyl)allylsilane, dichloro(benzyl)allylsilane, and dibromo(benzyl)allylsilane.

Other dihalogenated silane compounds are exemplified by dihalogenated di($C_{1-10}$ alkyl)silane compounds such as difluoro(dimethyl)silane, dichloro(dimethyl)silane, dibromo(dimethyl)silane, difluoro(diethyl)silane, dichloro(diethyl)silane, dibromo(diethyl)silane, difluoro(dipropyl)silane, dichloro(dipropyl)silane, dibromo(dipropyl)silane, difluoro(diburyl)silane, dichloro(diburyl)silane, and dibromo(diburyl)silane; dihalogenated di($C_{6-14}$ aryl)silane compounds such as difluoro(diphenyl)silane, dichloro(diphenyl)silane, dibromo(diphenyl)silane, difluoro(dinaphthyl)silane, dichloro(dinaphthyl)silane, and dibromo(dinaphthyl)silane; dihalogenated di($C_{7-15}$ aralkyl)silane compounds such as difluoro(dibenzyl)silane, dichloro(dibenzyl)silane, and dibromo(dibenzyl)silane; dihalogenated ($C_{1-10}$ alkyl)($C_{6-14}$ aryl)silane compounds such as difluoro(methyl)(phenyl)silane, difluoro(ethyl)(phenyl)silane, difluoro(propyl)(phenyl)silane, difluoro(butyl)phenylsilane, dichloro(methyl)phenylsilane, dichloro(ethyl)phenylsilane, dichloro(propyl)phenylsilane, dichloro(butyl)phenylsilane, dibromo(methyl)naphthylsilane, dibromo(ethyl)naphthylsilane, dibromo(propyl)naphthylsilane, and dibromo(butyl)naphthylsilane; and dihalogenated ($C_{1-10}$ alkyl)($C_{7-15}$ aralkyl)silane compounds such as difluoro(methyl)benzylsilane, difluoro(ethyl)benzylsilane, difluoro(propyl)benzylsilane, difluoro(butyl)benzylsilane, dichloro(methyl)benzylsilane, dichloro(ethyl)benzylsilane, dichloro(propyl)benzylsilane, dichloro(butyl)benzylsilane, dibromo(methyl)benzylsilane, dibromo(ethyl)benzylsilane, dibromo(propyl)benzylsilane, and dibromo(butyl)benzylsilane.

H-type dihydroxysilane compounds are exemplified by dihydroxysilane (including two hydrogen atoms); and dihydroxysilane compounds including one hydrogen atom, such as methyldihydroxysilane, ethyldihydroxysilane, propyldihydroxysilane, butyldihydroxysilane, phenyldihydroxysilane, naphthyldihydroxysilane, and benzyldihydroxysilane.

Vinyl-type dihydroxysilane compounds are exemplified by di($C_{2-10}$ alkenyl)dihydroxysilane compounds such as divinyldihydroxysilane, diallyldihydroxysilane, di(2-butenyl)dihydroxysilane, and di(2-pentanyl)dihydroxysilane; ($C_{1-10}$ alkyl)($C_{2-10}$ alkenyl)dihydroxysilane compounds such as methyl(vinyl)dihydroxysilane, ethyl(vinyl)dihydroxysilane, propyl(vinyl)dihydroxysilane, butyl(vinyl)dihydroxysilane, methyl(allyl)dihydroxysilane, ethyl(allyl)dihydroxysilane, propyl(allyl)dihydroxysilane, and butyl(allyl)dihydroxysilane; ($C_{6-14}$ aryl)($C_{2-10}$ alkenyl)dihydroxysilane compounds such as phenyl(vinyl)dihydroxysilane, naphthyl(vinyl)dihydroxysilane, phenyl(allyl)dihydroxysilane, and naphthyl(allyl)dihydroxysilane; ($C_{7-15}$ aralkyl)($C_{2-10}$ alkenyl)dihydroxysilane compounds such as benzyl(vinyl)dihydroxysilane and benzyl(allyl)dihydroxysilane.

Other dihydroxysilane compounds are exemplified by di($C_{1-10}$ alkyl)dihydroxysilane compounds such as dimethyldihydroxysilane, diethyldihydroxysilane, dipropyldihydroxysilane, and dibutyldihydroxysilane; di($C_{6-14}$ aryl)dihydroxysilane compounds such as diphenyldihydroxysilane and dinaphthyldihydroxysilane; di($C_{7-15}$ aralkyl)dihydroxysilane compounds such as dibenzyldihydroxysilane; ($C_{1-10}$ alkyl)($C_{6-14}$ aryl)dihydroxysilane compounds such as methyl(phenyl)dihydroxysilane, ethyl(phenyl)dihydroxysilane, propyl(phenyl)dihydroxysilane, butyl(phenyl)dihydroxysilane, methyl(naphthyl)dihydroxysilane, ethyl(naphthyl)dihydroxysilane, propyl(naphthyl)dihydroxysilane, and butyl (naphthyl)dihydroxysilane; and ($C_{1-10}$ alkyl)($C_{7-15}$ aralkyl)dihydroxysilanes such as methyl(benzyl)dihydroxysilane, ethyl(benzyl)dihydroxysilane, propyl(benzyl)dihydroxysilane, and butyl(benzyl)dihydroxysilane. Each of different compounds as exemplified above may be used alone or in combination as the silane compound (S1).

As for $R^1$ and $R^2$ in the silane compound (S1) represented by Formula (1), $C_{1-5}$ alkyl groups are preferred as the $C_{1-10}$ alkyl group; and $C_{2-5}$ alkenyl groups are preferred as the $C_{2-10}$ alkenyl group. $R^1$ and $R^2$ are each independently preferably any of methyl, ethyl, phenyl, vinyl, and allyl groups for satisfactory resistance to thermal yellowing; and are more preferably phenyl groups for satisfactory hydrolysis resistance.

Of $C_{1-10}$ alkoxy groups as $X^1$ and $X^2$ in Formula (1), $C_{1-6}$ alkoxy groups are preferred. For good availability, $X^1$ and $X^2$ are preferably independently any of methoxy group, ethoxy group, chlorine atom, bromine atom, and hydroxyl group; of which methoxy and ethoxy groups are more preferred for satisfactory stability before reaction.

Of the silane compounds, preferred as the silane compound (S1) are di($C_{1-10}$ alkyl)di($C_{1-12}$ alkoxy)silanes (of which di($C_{1-5}$ alkyl)di($C_{1-6}$ alkoxy)silanes are more preferred); and di($C_{6-14}$ aryl)di($C_{1-10}$ alkoxy)silanes (of which diphenyldi($C_{1-6}$ alkoxy)silanes are more preferred). Among them, particularly preferably usable is dimethyldimethoxysilane, diethyldimethoxysilane, diphenyldimethoxysilane, divinyldimethoxysilane, diallyldimethoxysilane, dimethyldiethoxysilane, diethyldiethoxysilane, diphenyldiethoxysilane, divinyldiethoxysilane, or diallyldiethoxysilane.

[Monofunctional Silane Compound (S2)]

A monofunctional silane compound (S2) for use in the reaction to form a metallosiloxane compound (A) according to the present invention is represented by following Formula (2)

[Chem. 6]

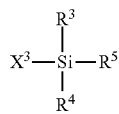

(2)

wherein $R^3$, $R^4$, and $R^5$ are the same as or different from one another and each represent a hydrogen atom, a $C_{1-10}$ alkyl group, a $C_{2-10}$ alkenyl group, a $C_{6-14}$ aryl group, or a $C_{7-15}$ aralkyl group; and $X^3$ represents a $C_{1-10}$ alkoxy group, a halogen atom, or a hydroxyl group.

The monofunctional silane compound (S2) may be any of known monoalkoxysilane compounds, monohalogenated silane compounds, and monohydroxysilane compounds customarily used in productions to form polysiloxanes and polyborosiloxanes.

The $C_{1-10}$ alkyl, $C_{2-10}$ alkenyl, $C_{6-14}$ aryl, and $C_{7-15}$ aralkyl groups as $R^3$, $R^4$, and $R^5$ in Formula (2) may be those listed as $R^1$ and $R^2$ in the bifunctional silane compounds (S1). The $C_{1-10}$ alkoxy group and halogen atom as $X^3$ may be those listed as $X^1$ and $X^2$ in the silane compounds (S1).

H-type monoalkoxysilane compounds are exemplified by ($C_{1-10}$ alkoxy)silane compounds including three hydrogen atoms, such as methoxysilane, ethoxysilane, propoxysilane, and butoxysilane; ($C_{1-10}$ alkoxy)silane compounds including two hydrogen atoms, such as methyl(methoxy)silane, methyl(ethoxy)silane, methyl(propoxy)silane, methyl(butoxy)silane, ethyl(methoxy)silane, ethyl(ethoxy)silane, ethyl(propoxy)silane, ethyl(butoxy)silane, propyl(methoxy)silane, propyl(ethoxy)silane, propyl(propoxy)silane, propyl(butoxy)silane, butyl(methoxy)silane, butyl(ethoxy)silane, butyl(propoxy)silane, butyl(butoxy)silane, phenyl(methoxy)silane, phenyl(ethoxy)silane, phenyl(propoxy)silane, phenyl(butoxy)silane, naphthyl(methoxy)silane, naphthyl(ethoxy)silane, naphthyl(propoxy)silane, naphthyl(butoxy)silane, benzyl(methoxy)silane, benzyl(ethoxy)silane, benzyl(propoxy)silane, and benzyl(butoxy)silane; di($C_{1-10}$ alkyl)($C_{1-10}$ alkoxy)silanes including one hydrogen atom, such as dimethyl(methoxy)silane, diethyl(methoxy)silane, dipropyl(methoxy)silane, dibutyl(methoxy)silane, dimethyl(ethoxy)silane, diethyl(ethoxy)silane, dipropyl(ethoxy)silane, dibutyl(ethoxy)silane, dimethyl(propoxy)silane, diethyl(propoxy)silane, dipropyl(propoxy)silane, dibutyl(propoxy)silane, dimethyl(butoxy)silane, diethyl(butoxy)silane, dipropyl(butoxy)silane, and dibutyl(butoxy)silane; di($C_{6-14}$ aryl)($C_{1-10}$ alkoxy)silanes including one hydrogen atom, such as diphenyl(methoxy)silane, dinaphthyl(methoxy)silane, diphenyl(ethoxy)silane, dinaphthyl(ethoxy)silane, diphenyl(propoxy)silane, dinaphthyl(propoxy)silane, diphenyl(butoxy)silane, and dinaphthyl(butoxy)silane; and di($C_{7-15}$ aralkyl)($C_{1-10}$ alkoxy)silanes including one hydrogen atom, such as dibenzyl(methoxy)silane, dibenzyl(ethoxy)silane, dibenzyl(propoxy)silane, and dibenzyl(butoxy)silane.

Vinyl-type monoalkoxysilane compounds are exemplified by tri($C_{2-10}$ alkenyl)($C_{1-10}$ alkoxy)silane compounds such as trivinyl(methoxy)silane, trivinyl(ethoxy)silane, trivinyl(propoxy)silane, trivinyl(butoxy)silane, triallyl(methoxy)silane, triallyl(ethoxy)silane, triallyl(propoxy)silane, and triallyl(butoxy)silane; ($C_{1-10}$ alkyl)di($C_{2-10}$ alkenyl)($C_{1-10}$ alkoxy))silane compounds such as methyl(divinyl)methoxysilane, methyl(divinyl)ethoxysilane, methyl(divinyl)propoxysilane, methyl(divinyl)butoxysilane, ethyl(divinyl)methoxysilane, ethyl(divinyl)ethoxysilane, ethyl(divinyl)propoxysilane, ethyl(divinyl)butoxysilane, propyl(divinyl)methoxysilane, propyl(divinyl)ethoxysilane, propyl(divinyl)propoxysilane, propyl(divinyl)butoxysilane, butyl(divinyl)methoxysilane, butyl(divinyl)ethoxysilane, butyl(divinyl)propoxysilane, butyl(divinyl)butoxysilane, methyl(diallyl)methoxysilane, methyl(diallyl)ethoxysilane, methyl(diallyl)propoxysilane, methyl(diallyl)butoxysilane, ethyl(diallyl)methoxysilane, ethyl(diallyl)ethoxysilane, ethyl(diallyl)propoxysilane, ethyl(diallyl)butoxysilane, propyl(diallyl)methoxysilane, propyl(diallyl)ethoxysilane, propyl(diallyl)propoxysilane, propyl(diallyl)butoxysilane, butyl(diallyl)methoxysilane, butyl(diallyl)ethoxysilane, butyl(diallyl)propoxysilane, and butyl(diallyl)butoxysilane; ($C_{6-14}$ aryl)di($C_{2-10}$ alkenyl)($C_{1-10}$ alkoxy)silanes such as phenyl(divinyl)methoxysilane, phenyl(divinyl)ethoxysilane, phenyl(divinyl)propoxysilane, phenyl(divinyl)butoxysilane, naphthyl(divinyl)methoxysilane, naphthyl(divinyl)ethoxysilane, naphthyl(divinyl)propoxysilane, naphthyl(divinyl)butoxysilane, phenyl(diallyl)methoxysilane, phenyl(diallyl)ethoxysilane, phenyl(diallyl)propoxysilane, phenyl(diallyl)butoxysilane, naphthyl(diallyl)methoxysilane, naphthyl(diallyl)ethoxysilane, naphthyl(diallyl)propoxysilane, and naphthyl(diallyl)butoxysilane; and ($C_{7-15}$ aralkyl)di($C_{2-10}$ alkenyl)($C_{1-10}$ alkoxy)silane compounds such as benzyl(divinyl)methoxysilane, benzyl(divinyl)ethoxysilane, benzyl(divinyl)propoxysilane, benzyl(divinyl)butoxysilane, benzyl(diallyl)methoxysilane, benzyl(diallyl)ethoxysilane, benzyl(diallyl)propoxysilane, and benzyl(diallyl)butoxysilane.

Vinyl-type monoalkoxysilane compounds are further exemplified by di($C_{1-10}$ alkyl)($C_{2-10}$ alkenyl)($C_{1-10}$ alkoxy)silane compounds such as dimethyl(vinyl)methoxysilane, diethyl(vinyl)methoxysilane, dipropyl(vinyl)methoxysilane, dibutyl(vinyl)methoxysilane, dimethyl(vinyl)ethoxysilane, diethyl(vinyl)ethoxysilane, dipropyl(vinyl)ethoxysilane, dibutyl(vinyl)ethoxysilane, dimethyl(vinyl)propoxysilane, diethyl(vinyl)propoxysilane, dipropyl(vinyl)propoxysilane, dibutyl(vinyl)propoxysilane, dimethyl(vinyl)butoxysilane, diethyl(vinyl)butoxysilane, dipropyl(vinyl)butoxysilane, dibutyl(vinyl)butoxysilane, dimethyl(allyl)methoxysilane, diethyl(allyl)methoxysilane, dipropyl(allyl)methoxysilane, dibutyl(allyl)methoxysilane, dimethyl(allyl)ethoxysilane, diethyl(allyl)ethoxysilane, dipropyl(allyl)ethoxysilane, dibutyl(allyl)ethoxysilane, dimethyl(allyl)propoxysilane, diethyl(allyl)propoxysilane, dipropyl(allyl)propoxysilane, dibutyl(allyl)propoxysilane, dimethyl(allyl)butoxysilane, diethyl(allyl)butoxysilane, dipropyl(allyl)butoxysilane, and dibutyl(allyl)butoxysilane; di($C_{6-14}$ aryl)($C_{2-10}$ alkenyl) ($C_{1-10}$ alkoxy)silane compounds such as diphenyl(vinyl) methoxysilane, dinaphthyl(vinyl)methoxysilane, diphenyl (vinyl)ethoxysilane, dinaphthyl(vinyl)ethoxysilane, diphenyl(vinyl)propoxysilane, dinaphthyl(vinyl)propoxysilane, diphenyl(vinyl)butoxysilane, dinaphthyl(vinyl)butoxysilane, diphenyl(allyl)methoxysilane, dinaphthyl(allyl)methoxysilane, diphenyl(allyl)ethoxysilane, dinaphthyl(allyl)ethoxysilane, diphenyl(allyl)propoxysilane, dinaphthyl(allyl)propoxysilane, diphenyl(allyl)butoxysilane, and dinaphthyl (allyl)butoxysilane; and di($C_{7-15}$ aralkyl)($C_{2-10}$ alkenyl) ($C_{1-10}$ alkoxy)silane compounds such as dibenzyl(vinyl) methoxysilane, dibenzyl(vinyl)ethoxysilane, dibenzyl(vinyl) propoxysilane, dibenzyl(vinyl)butoxysilane, dibenzyl(allyl) methoxysilane, dibenzyl(allyl)ethoxysilane, dibenzyl(allyl) propoxysilane, and dibenzyl(allyl)butoxysilane.

Other monoalkoxysilane compounds are exemplified by trimethyl(methoxy)silane, trimethyl(ethoxy)silane, triphenyl (methoxy)silane, triphenyl(ethoxy)silane, phenyl(dimethyl) methoxysilane, phenyl(dimethyl)ethoxysilane, phenyl(diethyl)methoxysilane, phenyl(diethyl)ethoxysilane, diphenyl (methyl)methoxysilane, diphenyl(methyl)ethoxysilane, diphenyl(ethyl)methoxysilane, and diphenyl(ethyl)ethoxysilane.

H-type monohalogenated silane compounds are exemplified by monohalogenated silane compounds including three hydrogen atoms, such as monofluorosilane, monochlorosilane, and monobromosilane; monohalogenated silane compounds including two hydrogen atoms, such as fluoro(methyl)silane, chloro(methyl)silane, bromo(methyl)silane, fluoro (ethyl)silane, chloro(ethyl)silane, bromo(ethyl)silane, fluoro (propyl)silane, chloro(propyl)silane, bromo(propyl)silane, fluoro(butyl)silane, chloro(butyl)silane, bromo(butyl)silane, fluoro(phenyl)silane, chloro(phenyl)silane, bromo(phenyl) silane, fluoro(naphthyl)silane, chloro(naphthyl)silane, bromo(naphthyl)silane, fluoro(benzyl)silane, chloro(benzyl)silane, and bromo(benzyl)silane; monohalogenated di($C_{1-10}$ alkyl)silane compounds including one hydrogen atom, such as fluoro(dimethyl)silane, chloro(dimethyl)silane, bromo (dimethyl)silane, fluoro(diethyl)silane, chloro(diethyl)silane, bromo(diethyl)silane, fluoro(dipropyl)silane, chloro (dipropyl)silane, bromo(dipropyl)silane, fluoro(diburyl) silane, chloro(diburyl)silane, and bromo(diburyl)silane; monohalogenated di($C_{6-14}$ aryl)silane compounds including one hydrogen atom, such as fluoro(diphenyl)silane, chloro (diphenyl)silane, bromo(diphenyl)silane, fluoro(dinaphthyl) silane, chloro(dinaphthyl)silane, and bromo(dinaphthyl)silane; monohalogenated di($C_{7-15}$ aralkyl)silane compounds including one hydrogen atom, such as fluoro(dibenzyl)silane, chloro(dibenzyl)silane, and bromo (dibenzyl)silane; monohalogenated ($C_{1-10}$ alkyl)($C_{6-14}$ aryl)silane compounds including one hydrogen atom, such as fluoro(methyl)phenylsilane, fluoro(ethyl)phenylsilane, fluoro(propyl)phenylsilane, fluoro(butyl)phenylsilane, chloro(methyl)phenylsilane, chloro(ethyl)phenylsilane, chloro(propyl)phenylsilane, chloro(butyl)phenylsilane, bromo(methyl)naphthylsilane, bromo (ethyl)naphthylsilane, bromo(propyl)naphthylsilane, and bromo(butyl)naphthylsilane; and monohalogenated ($C_{1-10}$ alkyl)($C_{7-15}$ aralkyl)silane compounds including one hydrogen atom, such as fluoro(methyl)benzylsilane, fluoro(ethyl) benzylsilane, fluoro(propyl)benzylsilane, fluoro(butyl)benzylsilane, chloro(methyl)benzylsilane, chloro(ethyl) benzylsilane, chloro(propyl)benzylsilane, chloro(butyl) benzylsilane, bromo(methyl)benzylsilane, bromo(ethyl) benzylsilane, bromo(propyl)benzylsilane, and bromo(butyl) benzylsilane.

Vinyl-type monohalogenated silane compounds are exemplified by monohalogenated tri($C_{2-10}$ alkenyl)silane compounds such as fluorotrivinylsilane, chlorotrivinylsilane, bromotrivinylsilane, fluorotriallylsilane, chlorotriallylsilane, and bromotriallylsilane; monohalogenated ($C_{1-10}$ alkyl)di ($C_{2-10}$ alkenyl)silane compounds such as fluoro(methyl)divinylsilane, chloro(methyl)divinylsilane, bromo(methyl)divinylsilane, fluoro(ethyl)divinylsilane, chloro(ethyl) divinylsilane, bromo(ethyl)divinylsilane, fluoro(propyl) divinylsilane, chloro(propyl)divinylsilane, bromo(propyl) divinylsilane, fluoro(butyl)divinylsilane, chloro(butyl) divinylsilane, bromo(butyl)divinylsilane, fluoro(methyl) diallylsilane, chloro(methyl)diallylsilane, bromo(methyl) diallylsilane, fluoro(ethyl)diallylsilane, chloro(ethyl) diallylsilane, bromo(ethyl)diallylsilane, fluoro(propyl) diallylsilane, chloro(propyl)diallylsilane, bromo(propyl) diallylsilane, fluoro(butyl)diallylsilane, chloro(butyl) diallylsilane, and bromo(butyl)diallylsilane; monohalogenated ($C_{6-14}$ aryl)di($C_{2-10}$ alkenyl)silane compounds such as fluoro(phenyl)divinylsilane, chloro(phenyl) divinylsilane, bromo(phenyl)divinylsilane, fluoro(naphthyl) divinylsilane, chloro(naphthyl)divinylsilane, bromo (naphthyl)divinylsilane, fluoro(phenyl)diallylsilane, chloro (phenyl)diallylsilane, bromo(phenyl)diallylsilane, fluoro (naphthyl)diallylsilane, chloro(naphthyl)diallylsilane, and bromo(naphthyl)diallylsilane; monohalogenated ($C_{7-15}$ aralkyl)di($C_{2-10}$ alkenyl)silane compounds such as fluoro (benzyl)divinylsilane, chloro(benzyl)divinylsilane, bromo (benzyl)divinylsilane, fluoro(benzyl)diallylsilane, chloro (benzyl)diallylsilane, and bromo(benzyl)diallylsilane.

Vinyl-type monohalogenated silane compounds are further exemplified by monohalogenated di($C_{1-10}$ alkyl)($C_{2-10}$ alkenyl)silane compounds such as fluoro(dimethyl)vinylsilane, chloro(dimethyl)vinylsilane, bromo(dimethyl)vinylsilane, fluoro(diethyl)vinylsilane, chloro(diethyl)vinylsilane, bromo (diethyl)vinylsilane, fluoro(dipropyl)vinylsilane, chloro (dipropyl)vinylsilane, bromo(dipropyl)vinylsilane, fluoro(diburyl)vinylsilane, chloro(diburyl)vinylsilane, bromo (diburyl)vinylsilane, fluoro(dimethyl)allylsilane, chloro (dimethyl)allylsilane, bromo(dimethyl)allylsilane, fluoro (diethyl)allylsilane, chloro(diethyl)allylsilane, bromo (diethyl)allylsilane, fluoro(dipropyl)allylsilane, chloro (dipropyl)allylsilane, bromo(dipropyl)allylsilane, fluoro (diburyl)allylsilane, chloro(diburyl)allylsilane, and bromo (diburyl)allylsilane; monohalogenated di($C_{6-14}$ aryl)($C_{2-10}$ alkenyl)silane compounds such as fluoro(diphenyl)vinylsilane, chloro(diphenyl)vinylsilane, bromo(diphenyl)vinylsilane, fluoro(dinaphthyl)vinylsilane, chloro(dinaphthyl)vinylsilane, bromo(dinaphthyl)vinylsilane, fluoro(diphenyl) allylsilane, chloro(diphenyl)allylsilane, bromo(diphenyl) allylsilane, fluoro(dinaphthyl)allylsilane, chloro(dinaphthyl) allylsilane, and bromo(dinaphthyl)allylsilane; monohalogenated di($C_{7-15}$ aralkyl)($C_{2-10}$ alkenyl)silane compounds such as fluoro(dibenzyl)vinylsilane, chloro (dibenzyl)vinylsilane, bromo(dibenzyl)vinylsilane, fluoro(dibenzyl)allylsilane, chloro(dibenzyl)allylsilane, and bromo(dibenzyl)allylsilane; monohalogenated ($C_{1-10}$ alkyl)($C_{6-14}$ aryl)($C_{2-10}$ alkenyl)silane compounds such as fluoro(methyl)(phenyl)vinylsilane, fluoro(ethyl)(phenyl)vinylsilane, fluoro(propyl)(phenyl)vinylsilane, fluoro(butyl)(phenyl)vinylsilane, chloro(methyl)(phenyl)vinylsilane, chloro(ethyl)(phenyl)vinylsilane, chloro(propyl)(phenyl)vinylsilane, chloro(butyl)(phenyl)vinylsilane, bromo(methyl)(naphthyl)vinylsilane, bromo(ethyl)(naphthyl)vinylsilane, bromo(propyl)(naphthyl)vinylsilane, bromo(butyl)(naphthyl)vinylsilane, fluoro(methyl)(phenyl)allylsilane, fluoro(ethyl)(phenyl)allylsilane, fluoro(propyl)(phenyl)allylsilane, fluoro(butyl)(phenyl)allylsilane, chloro(methyl)(phenyl)allylsilane, chloro(ethyl)(phenyl)allylsilane, chloro(propyl)(phenyl)allylsilane, chloro(butyl)(phenyl)allylsilane, bromo(methyl)(naphthyl)allylsilane, bromo(ethyl)(naphthyl)allylsilane, bromo(propyl)(naphthyl)allylsilane, and bromo(butyl)(naphthyl)allylsilane; and monohalogenated ($C_{1-10}$ alkyl)($C_{7-15}$ aralkyl)($C_{2-10}$ alkenyl)silane compounds such as fluoro(methyl)benzylvinylsilane, fluoro(ethyl)(benzyl)vinylsilane, fluoro(propyl)(benzyl)vinylsilane, fluoro(butyl)(benzyl)vinylsilane, chloro(methyl)(benzyl)vinylsilane, chloro(ethyl)(benzyl)vinylsilane, chloro(propyl)(benzyl)vinylsilane, chloro(butyl)(benzyl)vinylsilane, bromo(methyl)(benzyl)vinylsilane, bromo(ethyl)(benzyl)vinylsilane, bromo(propyl)(benzyl)vinylsilane, bromo(butyl)(benzyl)vinylsilane, fluoro(methyl)(benzyl)allylsilane, fluoro(ethyl)(benzyl)allylsilane, fluoro(propyl)(benzyl)allylsilane, fluoro(butyl)(benzyl)allylsilane, chloro(methyl)benzylallylsilane, chloro(ethyl)(benzyl)allylsilane, chloro(propyl)(benzyl)allylsilane, chloro(butyl)(benzyl)allylsilane, bromo(methyl)benzylallylsilane, bromo (ethyl)(benzyl)allylsilane, bromo(propyl)(benzyl)allylsilane, and bromo(butyl)(benzyl)allylsilane.

Other monohalogenated silane compounds are exemplified by fluoro(trimethyl)silane, chloro(trimethyl)silane, bromo(trimethyl)silane, fluoro(triphenyl)silane, chloro(triphenyl)silane, bromo(triphenyl)silane, fluoro(phenyl)dimethylsilane, chloro(phenyl)dimethylsilane, bromo(phenyl)dimethylsilane, fluoro(phenyl)diethylsilane, chloro(phenyl)diethylsilane, bromo(phenyl)diethylsilane, fluoro(diphenyl)methylsilane, chloro(diphenyl)methylsilane, bromo(diphenyl)methylsilane, fluoro(diphenyl)ethylsilane, chloro(diphenyl)ethylsilane, and bromo(diphenyl)ethylsilane.

H-type monohydroxysilane compounds are exemplified by monohydroxysilane (including three hydrogen atoms); hydroxysilane compounds including two hydrogen atoms, such as methylhydroxysilane, ethylhydroxysilane, propylhydroxysilane, butylhydroxysilane, phenylhydroxysilane, naphthylhydroxysilane, and benzylhydroxysilane; di($C_{1-10}$ alkyl)hydroxysilane compounds including one hydrogen atom, such as dimethylhydroxysilane, diethylhydroxysilane, dipropylhydroxysilane, and dibutylhydroxysilane; di($C_{6-14}$ aryl)hydroxysilane compounds including one hydrogen atom, such as diphenylhydroxysilane and dinaphthylhydroxysilane; di($C_{7-15}$ aralkyl)hydroxysilane compounds including one hydrogen atom, such as dibenzylhydroxysilane; ($C_{1-10}$ alkyl)($C_{6-14}$ aryl)hydroxysilane compounds including one hydrogen atom, such as methyl(phenyl)hydroxysilane, ethyl(phenyl)hydroxysilane, propyl(phenyl)hydroxysilane, butyl(phenyl)hydroxysilane, methyl(naphthyl)hydroxysilane, ethyl(naphthyl)hydroxysilane, propyl(naphthyl)hydroxysilane, and butyl(naphthyl)hydroxysilane; and ($C_{1-10}$ alkyl)($C_{7-15}$ aralkyl)hydroxysilane compounds including one hydrogen atom, such as methyl(benzyl)hydroxysilane, ethyl(benzyl)hydroxysilane, propyl(benzyl)hydroxysilane, and butyl(benzyl)hydroxysilane.

Vinyl-type monohydroxysilane compounds are exemplified by tri($C_{2-10}$ alkenyl)hydroxysilane compounds such as trivinylhydroxysilane and triallylhydroxysilane; ($C_{1-10}$ alkyl)di($C_{2-10}$ alkenyl)hydroxysilane compounds such as methyl(divinyl)hydroxysilane, ethyl(divinyl)hydroxysilane, propyl(divinyl)hydroxysilane, butyl(divinyl)hydroxysilane, methyl(diallyl)hydroxysilane, ethyl(diallyl)hydroxysilane, propyl(diallyl)hydroxysilane, and butyl(diallyl)hydroxysilane; ($C_{6-14}$ aryl)di($C_{2-10}$ alkenyl)hydroxysilane compounds such as phenyl(divinyl)hydroxysilane, naphthyl(divinyl)hydroxysilane, phenyl(diallyl)hydroxysilane, and naphthyl(diallyl)hydroxysilane; and ($C_{7-15}$ aralkyl)($C_{1-10}$ alkyl)di($C_{2-10}$ alkenyl)hydroxysilane compounds such as benzyl(divinyl)hydroxysilane and benzyl(diallyl)hydroxysilane.

Vinyl-type monohydroxysilane compounds are further exemplified by di($C_{1-10}$ alkyl)($C_{2-10}$ alkenyl)hydroxysilane compounds such as dimethyl(vinyl)hydroxysilane, diethyl(vinyl)hydroxysilane, dipropyl(vinyl)hydroxysilane, dibutyl(vinyl)hydroxysilane, dimethyl(allyl)hydroxysilane, diethyl(allyl)hydroxysilane, dipropyl(allyl)hydroxysilane, and dibutyl(allyl)hydroxysilane; di($C_{6-14}$ aryl)($C_{2-10}$ alkenyl)hydroxysilane compounds such as diphenyl(vinyl)hydroxysilane, dinaphthyl(vinyl)hydroxysilane, diphenyl(allyl)hydroxysilane, and dinaphthyl(allyl)hydroxysilane; di($C_{7-15}$ aralkyl)($C_{2-10}$ alkenyl)hydroxysilane compounds such as dibenzyl(vinyl)hydroxysilane and dibenzyl(allyl)hydroxysilane; ($C_{1-10}$ alkyl)($C_{6-14}$ aryl)($C_{2-10}$ alkenyl)hydroxysilane compounds such as methyl(phenyl)vinylhydroxysilane, ethyl(phenyl)vinylhydroxysilane, propyl(phenyl)vinylhydroxysilane, butyl(phenyl)vinylhydroxysilane, methyl(naphthyl)vinylhydroxysilane, ethyl(naphthyl)vinylhydroxysilane, propyl(naphthyl)vinylhydroxysilane, butyl(naphthyl)vinylhydroxysilane, methyl(phenyl)allylhydroxysilane, ethyl(phenyl)allylhydroxysilane, propyl(phenyl)allylhydroxysilane, butyl(phenyl)allylhydroxysilane, methyl(naphthyl)allylhydroxysilane, ethyl(naphthyl)allylhydroxysilane, propyl(naphthyl)allylhydroxysilane, and butyl(naphthyl)allylhydroxysilane; and ($C_{1-10}$ alkyl)($C_{7-15}$ aralkyl)($C_{2-10}$ alkenyl)hydroxysilane compounds such as methyl(benzyl)vinylhydroxysilane, ethyl(benzyl)vinylhydroxysilane, propyl(benzyl)vinylhydroxysilane, butyl(benzyl)vinylhydroxysilane, methyl(benzyl)allylhydroxysilane, ethyl(benzyl)allylhydroxysilane, propyl(benzyl)allylhydroxysilane, and butyl(benzyl)allylhydroxysilane.

Other monohydroxysilane compounds are exemplified by trimethylhydroxysilane, triphenylhydroxysilane, phenyl(dimethyl)hydroxysilane, phenyl(diethyl)hydroxysilane, diphenyl(methyl)hydroxysilane, and diphenyl(ethyl)hydroxysilane. Each of the exemplified compounds may be used alone or in combination as the silane compound (S2).

Of the $C_{1-10}$ alkyl groups as $R^3$, $R^4$, and $R^5$ in Formula (2), $C_{1-5}$ alkyl groups are preferred; and of the $C_{2-10}$ alkenyl groups, $C_{2-5}$ alkenyl groups are preferred. For satisfactory resistance to thermal yellowing, methyl, ethyl, phenyl, vinyl, and allyl groups are preferred as $R^3$, $R^4$, and $R^5$. Among them, phenyl group is more preferred for better hydrolysis resistance.

Of $C_{1-10}$ alkoxy groups as $X^3$ in Formula (2), $C_{1-6}$ alkoxy groups are preferred. $X^3$ is preferably methoxy group, ethoxy group, chlorine atom, bromine atom, or hydroxyl group for good availability; of which methoxy or ethoxy group is more preferred for better stability before reaction.

Of monofunctional silane compounds (S2), preferred are di($C_{1-10}$ alkyl)($C_{1-10}$ alkoxy)silanes (of which di($C_{1-5}$ alkyl)

($C_{1-6}$ alkoxy)silanes are more preferred); and di($C_{6-14}$ aryl)($C_{1-10}$ alkoxy)silanes (of which diphenyl($C_{1-6}$ alkoxy)silanes are more preferred). Specifically, the preferred monofunctional silane compounds (S2) are exemplified by dimethyl(methoxy)silane, diethyl(methoxy)silane, diphenyl(methoxy)silane, dimethyl(ethoxy)silane, diethyl(ethoxy)silane, diphenyl(ethoxy)silane, dimethyl(vinyl)methoxysilane, diethyl(vinyl)methoxysilane, diphenyl(vinyl)methoxysilane, dimethyl(vinyl)ethoxysilane, diethyl(vinyl)ethoxysilane, diphenyl(vinyl)ethoxysilane, dimethyl(allyl)methoxysilane, diethyl(allyl)methoxysilane, diphenyl(allyl)methoxysilane, dimethyl(allyl)ethoxysilane, diethyl(allyl)ethoxysilane, diphenyl(allyl)ethoxysilane, triphenyl(methoxy)silane, and triphenyl(ethoxy)silane.

The metallosiloxane compound according to the present invention has, per molecule, at least one Si—H bond or $C_{2-10}$ alkenyl group capable of undergoing hydrosilylation. To meet this, at least one of silane compounds to be used to form the metallosiloxane compound is an H-type silane compound having at least one Si—H bond per molecule, or a vinyl-type silane compound having at least one $C_{2-10}$ alkenyl group per molecule.

[Boron Compound (M)]

Boric acid compounds customarily used to form polyborosiloxanes may be used herein as the boron compound (M). Such boric acid compounds are exemplified by boron hydrides such as borane, diborane, tetraborane, pentaborane, and decaborane; boric acids such as orthoboric acid, metaboric acid, and tetraboric acid; borates such as nickel borate, magnesium borate, and manganese borate; boron oxides such as $B_2O_3$; nitrogen-containing compounds such as borazane, borazene, borazine, boronamide, and boronimide; halides such as $BF_3$, $BCl_3$, and tetrafluoroborates; and boric acid esters including alkyl borates such as methyl borate and ethyl borate, dialkyl borates such as dimethyl borate and diethyl borate, trialkyl borates such as trimethyl borate and triethyl borate, and aryl borates such as phenyl borate. Each of the exemplified compounds may be used alone or in combination as the boron compound (M).

Of boron compounds (M), preferred are those represented by following Formula (3):

[Chem. 7]

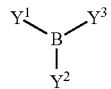

(3)

wherein $Y^1$, $Y^2$, and $Y^3$ are the same as or different from one another and each represent a $C_{1-12}$ alkoxy group, a halogen atom, or a hydroxyl group.

The $C_{1-12}$ alkoxy group as $Y^1$, $Y^2$, and $Y^3$ are exemplified by methoxy, ethoxy, propoxy, and butoxy groups, of which $C_{1-6}$ alkoxy groups are preferred. The halogen atom is exemplified by fluorine, chlorine, and bromine atoms.

Of such $C_{1-12}$ alkoxy groups as $Y^1$, $Y^2$, and $Y^3$, preferred are methoxy group, ethoxy group, propoxy group, butoxy group, chlorine atom, bromine atom, and hydroxyl group for good availability; of which propoxy group, butoxy group, and hydroxyl group are more preferred for better stability before reaction; and hydroxyl group is particularly preferred for easy reaction. Preferred boron compounds (M) include boron hydrides and boric acids (e.g., orthoboric acid) or salts thereof, of which boric acids are more preferred.

[$H_2O$]

When the boron compound (M) has one or more hydrolyzable substituents (e.g., alkoxy groups and halogen atoms), $H_2O$ may be added in a molar ratio (a) of half or more the total moles of the substituents. When the silane compound (S1), the silane compound (S2), and/or the boron compound (M) has one or more hydroxyl groups, $H_2O$ may be added in a reduced amount corresponding to the total moles of the hydroxyl groups, or no $H_2O$ may be used. Typically, no $H_2O$ may be used (i.e., a=0) when a boric acid having three hydroxyl groups is used as the boron compound (M).

[Catalyst]

The reaction may proceed without a catalyst, but an acid catalyst or base catalyst may be added to the reaction system according to necessity. The presence of an acid catalyst or base catalyst in the reaction system may generally significantly increase the reaction rate. The base includes inorganic bases and organic bases. The inorganic bases are exemplified by alkali metal hydroxides such as lithium hydroxide, sodium hydroxide, potassium hydroxide, and cesium hydrooxide; alkaline earth metal hydroxides such as magnesium hydroxide, calcium hydroxide, and barium hydroxide; alkali metal carbonates such as lithium carbonate, sodium carbonate, potassium carbonate, and cesium carbonate; alkaline earth metal carbonates such as magnesium carbonate; and alkali metal hydrogencarbonates such as lithium hydrogencarbonate, sodium hydrogencarbonate, potassium hydrogencarbonate, and cesium hydrogencarbonate.

The organic bases are exemplified by organic acid salts of alkali metals, such as lithium acetate, sodium acetate, potassium acetate, and cesium acetate (of which alkali metal acetates are preferred); organic acid salts of alkaline earth metals, such as magnesium acetate; alkyllithiums such as methyllithium and butyllithiums (e.g., n-butyllithium, s-butyllithium, and t-butyllithium); alkali metal alkoxides such as lithium methoxide, sodium methoxide, sodium ethoxide, sodium isopropoxide, and potassium ethoxide; alkali metal phenoxides such as sodium phenoxide; amines (including tertiary amines), such as triethylamine, N-methylpiperidine, 4-dimethylaminopyridine (DMAP), 1,8-diazabicyclo[5.4.0]-7-undecene (DBU), triethylenediamine(1,4-diazabicyclo[2.2.2]octane; DABCO), 1,5-diazabicyclo[4.3.0]-5-nonene (DBN), hexamethylenetetramine, tetramethylethylenediamine, trioctylamine, dimethylaniline, N-methylpyrrolidine, N-methylpiperidine, and 4-methylmorpholine; and nitrogen-containing heteroaromatic compounds such as pyridine, lutidine, picoline, imidazole, 2,2'-bipyridyl, and 1,10-phenanthroline. Each of different bases may be used alone or in combination. Among them, preferred are tertiary amines such as triethylamine and 4-dimethylaminopyridine; and nitrogen-containing heteroaromatic compounds such as pyridine, lutidine, and picoline.

The acid catalyst is exemplified by inorganic acids, organic acids, and solid acids. The inorganic acids are exemplified by sulfuric acid, hydrochloric acid, phosphoric acid, and nitric acid. The organic acids are exemplified by carboxylic acids including $C_{1-10}$ saturated or unsaturated mono- or poly-carboxylic acids such as acetic acid and propionic acid; sulfonic acids including $C_{1-6}$ alkanesulfonic acids such as methanesulfonic acid and ethanesulfonic acid, and aromatic sulfonic acids such as benzenesulfonic acid and p-toluenesulfonic acid; halogenated organic acids including halogenated carboxylic acids such as trifluoroacetic acid, and halogenated alkanesulfonic acids such as trifluoromethanesulfonic acid. The solid acids are exemplified by sulfuric acid salts such as calcium sulfate; metal oxides such as $SiO_2$ and $Al_2O_3$; zeolites such as Zeolites Y, X, and A having an acidic hydroxyl; and ion-exchange resins such as H-type and other cation-exchange resins.

Though not critical, the acid catalyst or base catalyst may be used in an amount of typically about 0.01 to about 5 moles, preferably about 0.1 to about 2 moles, and more preferably about 0.8 to about 1.2 moles, per 1 mole of hydroxyl groups in the reaction system. When neither acid catalyst nor base catalyst is used, the reaction may be accelerated by heating.

The reaction may be performed in the presence of a polymerization inhibitor. The reaction may be performed at a temperature that is suitably chosen according typically to types of reaction components and catalyst. For example, when vinylsilane is used, the reaction temperature may be about 20° C. to about 200° C., preferably about 20° C. to about 100° C., and more preferably about 40° C. to about 60° C. When a hydrosilane is used, the reaction temperature may be suitably chosen according typically to types of reaction components and catalyst and is typically about −78° C. to about 110° C., preferably about −30° C. to about 40° C., and more preferably about −10° C. to about 10° C. The reaction may be performed under normal atmospheric pressure, under reduced pressure, or under pressure (under a load). The reaction may be performed in any atmosphere, as long as not adversely affecting the reaction, such as air, nitrogen, or argon atmosphere. The reaction can be carried out according to any system such as batch, semi-batch, or continuous system.

After the completion of the reaction, a reaction product can be separated and purified by a separation procedure such as filtration, concentration, distillation, extraction, crystallization, recrystallization, or column chromatography, or a separation procedure as a combination of them. A reaction mixture after the reaction may be washed with an aqueous solvent such as water, a 1% to 7% dilute hydrochloric acid, or a 1% to 7% sodium bicarbonate water.

[Curable Resin Composition]

A curable resin composition according to an embodiment of the present invention is a curable resin composition including a compound having at least one Si—H bond and a compound having at least one $C_{2-10}$ alkenyl group and contains at least the metallosiloxane compound (A) and a hydrosilylation catalyst (C). The curable resin composition may contain the metallosiloxane compound (A) in a content of typically 30 to 99 percent by weight and preferably 40 to 60 percent by weight based on the total amount of the composition.

The curable resin composition according to the present invention may further contain a compound (B) having at least one Si—H bond or $C_{2-10}$ alkenyl group per molecule, which compound (B) is other than the metallosiloxane compound (A). When the metallosiloxane compound (A) is an H-type compound, the curable resin composition may contain a compound (B) having at least one $C_{2-10}$ alkenyl group per molecule [vinyl-type compound (B)]. When the metallosiloxane compound (A) is a vinyl-type compound, the curable resin composition may contain a compound (B) having at least one Si—H bond per molecule [H-type compound (B)].

[Compound (B) Having at Least One Si—H Bond or $C_{2-10}$ Alkenyl Group Per Molecule, Other than Metallosiloxane Compound (A)]

The H-type or vinyl-type compound (B) used herein may be any of H-type or vinyl-type polysiloxanes each having at least one Si—H bond or $C_{2-10}$ alkenyl group per molecule and having a principal chain including a siloxane bond (Si—O—Si). The $C_{2-10}$ alkenyl group is exemplified by those listed as $C_{2-10}$ alkenyl groups which may be contained in the silane compounds. Specifically, exemplary polysiloxanes include linear, branched chain, or cyclic siloxanes; and silicone resins each having a crosslinked three-dimensional structure.

Examples of the compound (B) include linear poly(dimethylsiloxane)s, hydrosilyl-containing silicones, vinyl-containing silicones, and other linear poly(dialkylsiloxane)s having one to ten (preferably two to five) Si—O units and having at least two selected from Si—H bonds and $C_{2-10}$ alkenyl groups per molecule, such as tetramethylsiloxane, tetramethyldivinylsiloxane, hexamethyltrisiloxane, hexamethyldivinyltrisiloxane, heptamethyltrisiloxane, heptamethyl(vinyl)trisiloxane, octamethyltetrasiloxane, octamethyldivinyltetrasiloxane, nonamethyltetrasiloxane, nonamethyl(vinyl)tetrasiloxane, nonamethyldivinyltetrasiloxane, decamethylpentasiloxane, decamethyldivinylpentasiloxane, undecamethylpentasiloxane, undecamethyl(vinyl)pentasiloxane, and decamethyldivinylpentasiloxane, of which linear poly(di($C_{1-10}$ alkyl)siloxane)s are preferred; and cyclic poly(dimethylsiloxane)s and other cyclic poly(dialkylsiloxane)s having two to ten (preferably two to five) Si—O units and having at least two selected from Si—H bonds and $C_{2-10}$ alkenyl groups per molecule, such as dimethylcyclotrisiloxane, dimethyldivinylcyclotrisiloxane, tetramethylcyclotetrasiloxane, tetramethyltetravinylcyclotetrasiloxane, trimethylcyclopentasiloxane, and trimethyltrivinylcyclopentasiloxane, of which cyclic poly(di($C_{1-10}$ alkyl)siloxane)s are preferred.

The polysiloxanes are further exemplified by compounds corresponding to the above-exemplified compounds, except with phenyl group or another aryl group (preferably $C_{6-20}$ aryl group) replacing all or part of alkyl group (e.g., methyl group) of the compounds. Such compounds are exemplified by polydiphenylsiloxanes and other linear or cyclic polydiarylsiloxanes having at least two selected from Si—H bonds and $C_{2-10}$ alkenyl groups per molecule, of which poly(di($C_{6-20}$ aryl)siloxane)s are preferred; poly(phenylmethylsiloxane)s and other linear or cyclic poly(alkylarylsiloxane)s having at least two selected from Si—H bonds and $C_{2-10}$ alkenyl groups per molecule, of which poly(($C_{1-10}$ alkyl)($C_{6-20}$ aryl)siloxane)s are preferred; and copolymers including any of the polyorganosiloxane units, such as dimethylsiloxane/methylvinylsiloxane copolymers, dimethylsiloxane/methylphenylsiloxane copolymers, dimethylsiloxane/methyl(3,3,3-trifluoropropyl)siloxane copolymers, and dimethylsiloxane/methylvinylsiloxane/methylphenylsiloxane copolymers. The exemplified polysiloxanes may each have one or more branched chains. The polysiloxanes usable herein are further exemplified by p-bis(dimethylsilyl)benzene and p-bis(dimethylvinylsilyl)benzene.

The polysiloxanes usable herein may have molecular weights of typically 1000000 to 1000 and preferably 100000 to 5000. A polysiloxane having a molecular weight within this range is advantageously satisfactorily compatible or miscible with the metallosiloxane.

Each of the polysiloxanes may be used alone or in combination as the compound (B). Of H-type compounds (B), preferred are tetramethyldisiloxane, hexamethyltrisiloxane, tetramethylcyclotetrasiloxane, hydrosilyl-containing silicones, and p-bis(dimethylsilyl)benzene. Of vinyl-type compounds (B), preferred are tetramethyldivinylsiloxane, hexamethyltrisiloxane, tetramethyltetravinylcyclotetrasiloxane, vinyl-containing silicones, and p-bis(dimethylvinylsilyl)benzene.

Exemplary compounds (B) usable herein further include compounds having at least one B—O—Si bond, such as boron dimethylvinylsiloxide and boron diethylvinylsiloxide.

The compound having at least one Si—H bond and the compound having at least one $C_{2-10}$ alkenyl group to be included in the curable resin composition according to the present invention may also be an H-type metallosiloxane compound (A) and a corresponding vinyl-type metallosiloxane compound (A).

The curable resin composition may contain the compound (B) typically in the range of 0 to 100 parts by weight and preferably 5 to 60 parts by weight per 100 parts by weight of the metallosiloxane compound (A). The compound (B), when contained within this range, may advantageously be satisfactorily miscible with the metallosiloxane to give a satisfactorily hard cured product. When the curable resin composition includes both an H-type metallosiloxane compound (A) and a vinyl-type metallosiloxane compound (A), the composition may employ no compound (B).

The curable resin composition according to the present invention may include any of other silane compounds corresponding to the exemplified H-type and vinyl-type compounds (B), except for containing neither Si—H bond nor alkenyl group.

The curable resin composition may contain silicon atoms typically in the range of 10 to 30 percent by weight and preferably 10 to 20 percent by weight. The curable resin composition may contain boron atoms typically in the range of 1 to 10 percent by weight and preferably 1 to 5 percent by weight. The curable resin composition, when containing silicon atoms and boron atoms in contents within these ranges, can give, through curing, a cured product having better resistance to thermal yellowing.

[Hydrosilylation Catalyst (C)]

A hydrosilylation catalyst (C) contained in the curable resin composition according to the present invention is exemplified by known catalysts for hydrosilylation, such as platinum, rhodium, and palladium catalysts. Specifically, such catalysts are exemplified by platinum catalysts such as platinum fine powder, platinum black, platinum supported on silica fine powder, platinum supported on activated carbon, chloroplatinic acid, complexes of chloroplatinic acid typically with an alcohol, aldehyde, or ketone, olefin complexes of platinum, carbonyl complexes of platinum (e.g., platinum-carbonylvinylmethyl complex), platinum-vinylmethylsiloxane complexes (e.g., platinum-divinyltetramethyldisiloxane complex and platinum-cyclovinylmethylsiloxane complex), platinum-phosphine complexes, and platinum-phosphite complexes; and palladium or rhodium catalysts corresponding to the platinum catalysts, except for containing palladium or rhodium atom instead of platinum atom. Each of them may be used alone or in combination. Among them, platinum-vinylmethylsiloxane complex is preferred for a satisfactory reaction rate.

The curable resin composition according to the present invention may contain the hydrosilylation catalyst (C) in such a content that the amount of platinum, palladium, or rhodium in the catalyst is in the range of preferably 0.01 to 1,000 ppm and more preferably 0.1 to 500 ppm by weight. When two or more different hydrosilylation catalysts (C) are used in combination, the content of the component (C) refers to the total content of the hydrosilylation catalysts (C). The curable resin composition, when containing the hydrosilylation catalyst(s) (C) within this range, may advantageously be protected from remarkably low crosslinking rate and from disadvantages (e.g., coloring) in the crosslinked product.

[Hydrosilylation Inhibitor]

The curable resin composition according to the present invention may contain a hydrosilylation inhibitor for the control of hydrosilylation rate. The hydrosilylation inhibitor is exemplified by alkyne alcohols such as 3-methyl-1-butyn-3-ol, 3,5-dimethyl-1-hexyn-3-ol, and phenylbutynol; ene-yne compounds such as 3-methyl-3-penten-1-yne and 3,5-dimethyl-3-hexen-1-yne; as well as 1,3,5,7-tetramethyl-1,3,5,7-tetravinylcyclotetrasiloxane, 1,3,5,7-tetramethyl-1,3,5,7-tetrahexenylcyclotetrasiloxane, and benzotriazole. The curable resin composition may contain the hydrosilylation inhibitor in a content of practically preferably 0.00001 to 5 parts by weight per 100 parts by weight of the composition, though the content may vary depending on crosslinking conditions of the composition.

[Solvent]

The hydrosilylation may be performed in the presence of a common known solvent which is exemplified by toluene, hexane, isopropanol, methyl isobutyl ketone, cyclopentanone, and propylene glycol monomethyl ether acetate.

[Inorganic Filler (D)]

The curable resin composition according to the present invention may further include an inorganic filler (D). The inorganic filler (D) is exemplified by, but not limited to, nanosilica, nanotitania, nanozirconia, carbon nanotubes, silica, alumina, mica, synthetic mica, talc, calcium oxide, calcium carbonate, zirconium oxide, titanium oxide, barium titanate, kaolin, bentonite, diatomaceous earth, boron nitride, aluminum nitride, silicon carbide, zinc oxide, cerium oxide, cesium oxide, magnesium oxide, glass beads, glass fibers, graphite, calcium hydroxide, magnesium hydroxide, aluminum hydroxide, and celluloses. Each of them may be used alone or in combination. These inorganic fillers (D) may be prepared by known processes such as flame hydrolysis, flame pyrolysis, and plasma process described in PCT International Publication Number WO 96/31572.

Preferred inorganic fillers (D) include stabilized colloidal nanodisperse sols of inorganic particles such as nanosilica, nanotitania, nanozirconia, and carbon nanotubes. They are available as commercial products such as silica sole from BAYER AG; $SnO_2$ sols from Goldschmidt AG; $TiO_2$ sols from Merck & Co., Inc.; $SiO_2$, $ZrO_2$, $Al_2O_3$, and $Sb_2O_3$ sols from Nissan Chemicals; and aerosil dispersions from Degussa AG. It is necessary that such inorganic fillers (D) do not block visible light.

Viscosity behavior of an inorganic filler (D) may be changed through surface modification. Surface modification of such particles can be performed with a known surface modifier. Exemplary surface modifiers usable herein include compounds capable of interacting with a functional group in the surface of the inorganic filler (D) (e.g., to form a covalent bond or a complex); and compounds capable of interacting with the polymer matrix thereof. The surface modifiers usable herein are exemplified by compounds having one or more functional groups per molecule. The functional groups are exemplified by carboxyl groups, (primary, secondary, or tertiary) amino groups, quaternary ammonium groups, carbonyl groups, glycidyl groups, vinyl groups, (meth)acryloxy groups, and mercapto groups. The surface modifier generally includes a low-molecular-weight organic compound which is liquid at a standard temperature and pressure and has carbon atoms in a number of 15 or less, preferably 10 or less, and particularly preferably 8 or less per molecule. The low-molecular-weight organic compound has a molecular weight of typically 500 or less, preferably 350 or less, and particularly preferably 200 or less.

Preferred surface modifiers include saturated or unsaturated mono- and poly-carboxylic acids having 1 to 12 carbon atoms, such as formic acid, acetic acid, propionic acid, butyric acid, pentanoic acid, hexanoic acid, acrylic acid, methacrylic acid, crotonic acid, citric acid, adipic acid, succinic acid, glutaric acid, oxalic acid, maleic acid, and fumaric acid, of which monocarboxylic acids are preferred; esters of these carboxylic acids, of which methyl methacrylate and other $C_{1-4}$ alkyl esters are preferred; amides; β-dicarbonyl compounds such as acetylacetone, 2,4-hexanedione, 3,5-heptanedione, acetoacetic acid, and $C_{1-4}$ alkylacetoacetic acids. Any of known or customary silane coupling agents may also be used as the surface modifier.

The inorganic filler (D) has a particle diameter of generally about 0.01 nm to about 200 µm, preferably about 0.1 nm to about 100 µm, and particularly preferably about 0.1 nm to about 50 µm.

The curable resin composition may contain the inorganic filler (D) in a content of preferably 1 to 2000 parts by weight and more preferably 10 to 1000 parts by weight per 100 parts by weight of the total content of the compound (A) and the compound (B); and in a content of typically 5 to 95 percent by weight and preferably 10 to 90 percent by weight based on the total amount of the curable resin composition.

[Silane Coupling Agent (E)]

For better adhesiveness with an adherend such as a substrate, the curable resin composition according to the present invention may further include a silane coupling agent (E). The silane coupling agent (E) is not limited and can be any of known or customary silane coupling agents. Such silane coupling agent (E) may be selected from among silane coupling agents that are relatively stable in an aqueous solution, such as tetramethoxysilane, tetraethoxysilane, methyltriethoxysilane, dimethyldiethoxysilane, methyltriethoxysilane, vinyltriethoxysilane, vinyltrimethoxysilane, vinyltris(methoxyethoxysilane), phenyltrimethoxysilane, diphenyldimethoxysilane, vinyltriacetoxysilane, γ-(meth)acryloxypropyltriethoxysilane, γ-(meth)acryloxypropyltrimethoxysilane, γ-(meth)acryloxypropyl(methyl)dimethoxysilane, γ-(meth)acryloxypropyl(methyl)diethoxysilane, 3-glycidoxypropyltrimethoxysilane, 3-glycidoxypropyl(methyl)dimethoxysilane, 3-glycidoxypropyltriethoxysilane, 3-glycidoxypropyl(methyl)diethoxysilane, 2-(3,4-epoxycyclohexyl)ethyltrimethoxysilane, p-styryltrimethoxysilane, 3-acryloxypropyltrimethoxysilane, N-(β-aminoethyl)-γ-aminopropyl(methyl)dimethoxysilane, N-β-aminoethyl)-γ-aminopropyl(methyl)diethoxysilane, N-β-aminoethyl)-γ-aminopropyltrimethoxysilane, N-β-aminoethyl)-γ-aminopropyltriethoxysilane, N-phenyl-γ-aminopropyltrimethoxysilane, γ-aminopropyltrimethoxysilane, γ-aminopropyltriethoxysilane, 3-mercaptopropyltrimethoxysilane, 3-mercaptopropyltriethoxysilane, 3-mercaptopropyl(methyl)dimethoxysilane, bis(triethoxysilylpropyl)tetrasulfide, and 3-isocyanatopropyltriethoxysilane.

The curable resin composition may contain the silane coupling agent (E) in an amount of preferably from about 0.1 to about 20 percent by weight, more preferably from 0.3 to 8 percent by weight, and furthermore preferably from 0.5 to 5 percent by weight based on the total amount of the curable resin composition. The silane coupling agent (E), if contained in an amount of less than 0.1 percent by weight, may insufficiently effectively contribute to crosslinking of resins, fail to give a dense film, exhibit insufficient coupling with a metallic base material, cause poor adhesion therewith, and often fail to provide desired alkali resistance and desired rust preventive activity. The silane coupling agent (E), if contained in an amount of more than 20 percent by weight, may cause the curable resin composition to suffer from, due to hydrolysis, significant deterioration in properties such as water resistance and alkali resistance, disadvantageously have insufficient film-formability, and cause economical disadvantages.

[Other Additives]

The curable resin composition according to the present invention may further include one or more customary additives as other optional components. The additives are exemplified by fillers including fine powders of organic resins such as silicone resins, epoxy resins, and fluorocarbon resins, and electroconductive powders of metals such as silver and copper; solvents; stabilizers such as antioxidants, ultraviolet absorbers, photostabilizers, and thermal stabilizers; flame retardants such as phosphorus-based, halogen-based, and inorganic flame retardants; flame retardant promoters; crosslinking agents; reinforcing materials such as other fillers; nucleating agents; coupling agents; agents; waxes; plasticizers; releasing agents; impact modifiers; hue modifiers; flow improvers; colorants such as dyestuffs and pigments; dispersing agents; antifoaming agents; defoaming agents; antimicrobial agents; antiseptic agents; viscosity modifiers; thickeners; leveling agents; ion adsorbents; and phosphors. Each of different additives may be used alone or in combination.

Curable resin compositions according to embodiments of the present invention are liquid at a temperature in the range of preferably 0° C. to 90° C., more preferably 0° C. to 40° C., and particularly preferably around room temperature (from about 0° C. to about 30° C.) and exhibit satisfactory workability upon encapsulation, sealing, and coating of electronic devices. The curable resin compositions are therefore usable typically as encapsulants or sealants for organic electroluminescent devices, LEDs, and other electronic components which require high refractive indices and low moisture permeability. The curable resin compositions are also usable as antireflective coating agents and adhesives for displays.

[Production Method of Curable Resin Composition]

A curable resin composition according to the present invention is available by uniformly mixing the components with one another. To give the curable resin composition according to the present invention, stirring, dissolution, mixing, and/or dispersion of the components is desirably performed using a common known mixing apparatus so as to give a mixture as uniform as possible. Such mixing apparatus is exemplified by planetary mixer/deaerators, homogenizers, planetary mixers, triple roll mills, and bead mills.

[Cured Product]

A curable resin composition according to the present invention may be cured by the application of light or heat. When cured by the application of light, the composition may be cured by the light application at 1000 mJ/cm$^2$ or more from a mercury lamp. When cured by the application of heat, the composition may be cured at a temperature of 50° C. to 200° C., preferably 50° C. to 190° C., and more preferably 50° C. to 180° C. for a curing time of 10 to 600 minutes, preferably 10 to 480 minutes, and more preferably 15 to 360 minutes. The resin composition, if cured at a temperature and/or for a time shorter (lower) than the lower limit of the above range, may disadvantageously suffer from insufficient curing. In contrast, the resin composition, if cured at a temperature and/or for a time longer (higher) than the upper limit of the range, may disadvantageously decompose. While depending on various factors, curing conditions can be suitably controlled so that the curing time be short at a high curing temperature and be long at a low curing temperature. The curable resin composition according to the present invention, when cured, can give a cured product which has satisfactory transparency with less bubbles and is highly resistant to thermal yellowing. Such curable resin compositions according to embodiments of the present invention are usable as encapsulants, sealants, or coating agents typically for organic electroluminescent devices, LEDs, or displays.

EXAMPLES

The present invention will be illustrated in further detail with reference to several working examples below, which are by no means intended to limit the scope of the invention.

Example 1

In a glass flask equipped with a stirrer, a thermometer, and a Dimroth condenser, were placed 3.09 g (50 mmol) of boric acid and 18.03 g (150 mmol) of dimethyldimethoxysilane (D1052 supplied by Tokyo Chemical Industry Co., Ltd.), followed by stirring at 80° C. After leaving the flask standing to cool to room temperature, the mixture was combined with 6.18 g (100 mmol) of boric acid, 12.22 g (50 mmol) of dimethoxydiphenylsilane (D1731 supplied by Tokyo Chemical Industry Co., Ltd.) and 26.05 g (200 mmol) of dimethyl(vinyl)ethoxysilane (V0046 supplied by Tokyo Chemical Industry Co., Ltd.), followed by stirring at 80° C. for 3 hours. After the completion of reaction, the mixture was left standing to cool to room temperature, from which unreacted components and volatile components were removed on an evaporator, and thereby yielded a liquid vinyl-containing boromethylphenylsiloxane.

Example 2

A hydrosilyl-containing boromethylphenylsiloxane was prepared by the procedure of Example 1, except for using 20.85 g (200 mmol) of dimethyl(ethoxy)silane (SIV9072.0 supplied by Gelest, Inc.) instead of 26.05 g (200 mmol) of dimethyl(vinyl)ethoxysilane.

Example 3

To 0.20 g of the liquid vinyl-containing boromethylphenylsiloxane prepared in Example 1, were sequentially added 0.4 µL of a platinum catalyst (326-49351 supplied by Wako Pure Chemical Industries, Ltd.) and 0.037 g of a hydrosilyl-containing silicone (HMS-64 supplied by Gelest, Inc., molecular weight: 55000 to 65000), followed by mixing. The resulting mixture was applied onto a glass plate and cured in an oven at 60° C. for one hour and subsequently at 120° C. for 3 hours to give a cured product. The cured product bore no bubble as observed, and remained colorless and transparent even when left stand in an oven at 180° C. for 500 hours or longer.

Example 4

A mixture was prepared by mixing 0.059 g of boron dimethylvinylsiloxide (AKB159.9 supplied by Gelest, Inc., molecular weight: 314) with 0.078 g of a vinyl-containing silicone (DMS-V21 supplied by Gelest, Inc., molecular weight: 6000) and further with 0.4 µL of a platinum catalyst (326-49351 supplied by Wako Pure Chemical Industries, Ltd.). The mixture was combined with 0.10 g of the liquid hydrosilyl-containing boromethylphenylsiloxane prepared in Example 2. The resulting mixture was applied onto a glass plate and cured in an oven at 60° C. for one hour and subsequently at 120° C. for 3 hours to give a cured product. The cured product bore no bubble as observed, and remained colorless and transparent even when left stand in an oven at 180° C. for 500 hours or longer.

INDUSTRIAL APPLICABILITY

Metallosiloxane compounds according to embodiments of the present invention give curable resin compositions which are resistant to outgassing upon curing and which give, through curing, cured products having satisfactory resistance to thermal yellowing. They are therefore useful typically as encapsulants, sealants, or heat-resisting hard coatings for LEDs and other electronic devices.

The invention claimed is:

1. A metallosiloxane compound as a metallosiloxane compound (A) prepared by reacting a silane compound (S1) represented by Formula (1), a silane compound (S2) represented by Formula (2), and a boron compound (M), or reacting the silane compound (S1), the silane compound (S2), the boron compound (M), and $H_2O$ in a molar ratio of [the silane compound (S1)]:[the silane compound (S2)]:[the boron compound (M)]:[$H_2O$] of n:m:k:a, where n, m, k, and a satisfy all conditions (i), (ii), and (iii), wherein the metallosiloxane compound has at least one Si—H bond or $C_{2-10}$ alkenyl group per molecule, Formula (1) expressed as follows:

[Chem. 1]

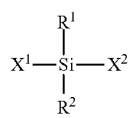

(1)

wherein $R^1$ and $R^2$ are the same as or different from each other and each represent a hydrogen atom, a $C_{1-10}$ alkyl group, a $C_{2-10}$ alkenyl group, a $C_{6-14}$ aryl group, or a $C_{7-15}$ aralkyl group; and $X^1$ and $X^2$ are the same as or different from each other and each represent a $C_{1-10}$ alkoxy group, a halogen atom, or a hydroxyl group, Formula (2) expressed as follows:

[Chem. 2]

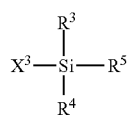

(2)

wherein $R^3$, $R^4$, and $R^5$ are the same as or different from one another and each represent a hydrogen atom, a $C_{1-10}$ alkyl group, a $C_{2-10}$ alkenyl group, a $C_{6-14}$ aryl group, or a $C_{7-15}$ aralkyl group; and $X^3$ represents a $C_{1-10}$ alkoxy group, a halogen atom, or a hydroxyl group, and the conditions (i), (ii), (iii) expressed as follows:
(i) n>0, m>0, k>0, a≥0;
(ii) m/n≥0.5; and
(iii) (n+m)/k≥1.8.

2. The metallosiloxane compound of claim 1, which is liquid at a temperature in a range from 0° C. to 90° C.

3. A curable resin composition comprising: a compound having at least one Si—H bond; and a compound having at least one $C_{2-10}$ alkenyl group, wherein the curable resin composition comprises at least the metallosiloxane compound (A) of one of claims 1 and 2; and a hydrosilylation catalyst (C).

4. The curable resin composition of claim 3, further comprising an inorganic filler (D).

5. The curable resin composition of claim 3, further comprising a silane coupling agent (E).

6. A cured product cured from a curable resin composition comprising:
a compound having at least one Si—H bond;
a compound having at least one $C_{2-10}$ alkenyl group; and
a hydrosilylation catalyst,
wherein the curable resin composition comprises at least a metallosiloxane compound (A) prepared by reacting a silane compound (S1) represented by Formula (1), a silane compound (S2) represented by Formula (2), and a boron compound (M), or reacting the silane compound (S 1), the silane compound (S2), the boron compound (M), and $H_2O$ in a molar ratio of [the silane compound (S1)]:[the silane compound (S2)]:[the boron compound (M)]:[$H_2O$] of n:m:k:a, where n, m, k, and a satisfy all conditions (i), (ii), and (iii), wherein the metallosiloxane compound has at least one Si—H bond or $C_{2-10}$ alkenyl group per molecule, Formula (1) expressed as follows:

[Chem. 1]

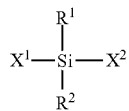

(1)

wherein $R^1$ and $R^2$ are the same as or different from each other and each represent a hydrogen atom, a $C_{1-10}$ alkyl group, a $C_{2-10}$ alkenyl group, a $C_{6-14}$ aryl group, or a $C_{7-15}$ aralkyl group; and $X^1$ and $X^2$ are the same as or different from each other and each represent a $C_{1-10}$ alkoxy group, a halogen atom, or a hydroxyl group, Formula (2) expressed as follows:

[Chem. 2]

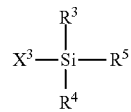

(2)

wherein $R^3$, $R^4$, and $R^5$ are the same as or different from one another and each represent a hydrogen atom, a $C_{1-10}$ alkyl group, a $C_{2-10}$ alkenyl group, a $C_{6-14}$ aryl group, or a $C_{7-15}$ aralkyl group; and $X^3$ represents a $C_{1-10}$ alkoxy group, a halogen atom, or a hydroxyl group, and the conditions (i), (ii), (iii) expressed as follows:
(i) n>0, m>0, k>0, a≥0;
(ii) m/n≥0.5; and
(iii) (n+m)/k≥1.8.

* * * * *